US008079953B2

(12) United States Patent  
Braun et al.

(10) Patent No.: US 8,079,953 B2  
(45) Date of Patent: Dec. 20, 2011

(54) GENERAL-PURPOSE MEDICAL INSTRUMENTATION

(75) Inventors: Jeffrey C. Braun, Ann Arbor, MI (US); Charles J. Jacobus, Ann Arbor, MI (US); Scott Booth, Ann Arbor, MI (US); Michael Suarez, Ypsilanti, MI (US); Derek Smith, Ann Arbor, MI (US); Jeff Hartnagle, Ann Arbor, MI (US); Glenn Leprell, Ypsilanti, MI (US)

(73) Assignee: Cybernet Systems Corporation, Ann Arbor, MI (US)

( * ) Notice: Subject to any disclaimer, the term of this patent is extended or adjusted under 35 U.S.C. 154(b) by 111 days.

(21) Appl. No.: 11/099,031

(22) Filed: Apr. 5, 2005

(65) Prior Publication Data

US 2006/0089541 A1    Apr. 27, 2006

Related U.S. Application Data

(63) Continuation of application No. 10/125,026, filed on Apr. 18, 2002, now Pat. No. 6,875,174, which is a continuation of application No. 09/519,115, filed on Mar. 6, 2000, now Pat. No. 6,375,614, which is a continuation of application No. 08/877,691, filed on Jun. 17, 1997, now Pat. No. 6,050,940.

(60) Provisional application No. 60/019,962, filed on Jun. 17, 1996.

(51) Int. Cl.  
*A61B 5/00* (2006.01)

(52) U.S. Cl. ........................................ 600/300; 128/920

(58) Field of Classification Search .................. 600/300  
See application file for complete search history.

(56) References Cited

U.S. PATENT DOCUMENTS

| 4,259,548 A | 3/1981 | Fahey et al. ..................... 379/38 |
| 4,731,726 A | 3/1988 | Allen, III ....................... 600/300 |
| 4,803,625 A * | 2/1989 | Fu et al. ......................... 600/483 |
| 4,838,275 A | 6/1989 | Lee ................................ 600/483 |
| 4,958,641 A | 9/1990 | Digby et al. .................. 600/515 |
| 4,967,756 A | 11/1990 | Hewitt ........................... 600/493 |
| 4,977,899 A | 12/1990 | Digby et al. .................. 600/515 |
| 5,016,172 A | 5/1991 | Dessertine .................... 600/300 |

(Continued)

FOREIGN PATENT DOCUMENTS

WO    WO 95/07048    *    3/1995

*Primary Examiner* — Henry M Johnson, III  
*Assistant Examiner* — Kai Rajan  
(74) *Attorney, Agent, or Firm* — Gifford, Krass, Sprinkle, Anderson & Citkowski, P.C.

(57) ABSTRACT

A general-purpose, low-cost system provides comprehensive physiological data collection, with extensive data object oriented programmability and configurability for a variety of medical as well as other analog data collection applications. In a preferred embodiment, programmable input signal acquisition and processing circuits are used so that virtually any analog and/or medical signal can be digitized from a common point of contact to a plurality of sensors. A general-purpose data routing and encapsulation architecture supports input tagging and standardized routing through modern packet switch networks, including the Internet; from one of multiple points of origin or patients, to one or multiple points of data analysis for physician review. The preferred architecture further supports multiple-site data buffering for redundancy and reliability, and real-time data collection, routing, and viewing (or slower than real-time processes when communications infrastructure is slower than the data collection rate). Routing and viewing stations allow for the insertion of automated analysis routines to aid in data encoding, analysis, viewing, and diagnosis.

6 Claims, 13 Drawing Sheets

U.S. PATENT DOCUMENTS

| | | | |
|---|---|---|---|
| 5,111,396 A | 5/1992 | Mills et al. | 600/508 |
| 5,228,450 A | 7/1993 | Sellers | 600/524 |
| 5,231,990 A | 8/1993 | Gauglitz | 600/510 |
| 5,262,943 A | 11/1993 | Thibado et al. | 600/300 |
| 5,307,263 A * | 4/1994 | Brown | 600/301 |
| 5,319,363 A * | 6/1994 | Welch et al. | 340/825.36 |
| 5,331,549 A | 7/1994 | Crawford, Jr. | 600/513 |
| 5,339,821 A | 8/1994 | Fujimoto | 600/513 |
| 5,375,604 A | 12/1994 | Kelly et al. | 600/484 |
| 5,390,238 A | 2/1995 | Kirk et al. | 379/106.02 |
| 5,410,471 A | 4/1995 | Alyfuku et al. | 600/300 |
| 5,434,611 A | 7/1995 | Tamura | 725/116 |
| 5,438,607 A | 8/1995 | Przygoda, Jr. et al. | 379/38 |
| 5,441,047 A | 8/1995 | David et al. | 600/483 |
| 5,458,123 A | 10/1995 | Unger | 600/509 |
| 5,488,412 A * | 1/1996 | Majeti et al. | 725/111 |
| 5,501,231 A | 3/1996 | Kaish | 600/538 |
| 5,502,726 A | 3/1996 | Fischer | 370/392 |
| 5,518,001 A | 5/1996 | Snell | 600/510 |
| 5,544,649 A | 8/1996 | David et al. | 600/301 |
| 5,549,117 A | 8/1996 | Tacklind et al. | 600/529 |
| 5,553,609 A | 9/1996 | Chen et al. | 600/301 |
| 5,558,638 A | 9/1996 | Evers et al. | 604/66 |
| 5,564,429 A * | 10/1996 | Bornn et al. | 600/508 |
| 5,576,952 A | 11/1996 | Stutman et al. | 600/300 |
| 5,586,257 A | 12/1996 | Perlman | 709/228 |
| 5,590,648 A | 1/1997 | Mitchell et al. | 600/301 |
| 5,613,495 A | 3/1997 | Mills et al. | 600/509 |
| 5,619,991 A | 4/1997 | Sloane | 600/300 |
| 5,640,953 A | 6/1997 | Bishop et al. | 600/300 |
| 5,642,731 A | 7/1997 | Kehr | 600/300 |
| 5,666,487 A | 9/1997 | Goodman et al. | 709/246 |
| 5,678,562 A | 10/1997 | Sellers | 128/904 |
| 5,687,734 A | 11/1997 | Dempsey et al. | 600/509 |
| 5,704,364 A | 1/1998 | Saltzstein et al. | 600/300 |
| 5,715,823 A | 2/1998 | Wood et al. | 600/437 |
| 5,727,002 A * | 3/1998 | Miller et al. | 714/748 |
| 5,732,696 A | 3/1998 | Rapoport et al. | 600/301 |
| 5,778,882 A | 7/1998 | Raymond et al. | 600/513 |
| 5,785,650 A | 7/1998 | Akasaka et al. | 600/300 |
| 5,807,245 A * | 9/1998 | Aldestam et al. | 600/300 |
| 5,862,803 A * | 1/1999 | Besson et al. | 600/508 |
| 5,897,493 A | 4/1999 | Brown | 600/300 |
| 5,899,855 A | 5/1999 | Brown | 600/301 |
| 5,913,310 A | 6/1999 | Brown | 128/897 |
| 5,918,603 A | 7/1999 | Brown | 128/897 |
| 5,941,829 A | 8/1999 | Saltzstein et al. | 600/509 |
| 6,001,065 A * | 12/1999 | DeVito | 600/544 |
| 6,023,686 A | 2/2000 | Brown | 705/37 |
| 6,213,942 B1 * | 4/2001 | Flach et al. | 600/300 |
| 6,375,614 B1 | 4/2002 | Braun et al. | 600/300 |
| 2001/0023315 A1 * | 9/2001 | Flach et al. | 600/300 |

* cited by examiner

GENERAL-PURPOSE MEDICAL INSTRUMENTATION

REFERENCE TO RELATED APPLICATION

This application is a continuation of U.S. patent application Ser. No. 10/125,026, filed Apr. 18, 2002, which is a continuation of U.S. patent application Ser. No. 09/519,115, filed Mar. 6, 2000, now U.S. Pat. No. 6,375,614, which is a continuation of U.S. patent application Ser. No. 08/877,691, filed Jun. 17, 1997, now U.S. Pat. No. 6,050,940, which claims priority from of U.S. provisional application Ser. No. 60/019,962, filed Jun. 17, 1996, the entire contents of each being incorporated herein by reference.

FIELD OF THE INVENTION

The present invention relates generally to medical instrumentation and, in particular, to apparatus and methods which support a wide variety of measurement, collection, communication, and analysis functions.

BACKGROUND OF THE INVENTION

There exists a need for comprehensive physiological monitoring in portable and remote settings. Current systems are generally large, costly, and inflexible, and although portable devices are now becoming available, they provide only limited, special-purpose capabilities. More specifically, existing medical instruments do not support multiple, programmable input channels which would allow any analog signal type (EEG, EMG, EKG, or higher-level signals) to be filtered, amplified, digitized, encapsulated, and routed through a complex digital network under programmed control, thereby offering a truly universal data core function.

At the same time, in the computer industry there has been a movement toward system interoperability through open systems protocols. This movement is being driven by TCP/IP, followed by X-windows (for transmission of windowed graphics), NFS (for file systems access), and new applications level protocols and file formats such as X.500, HTML, and SMTP. These protocols and file format standards have allowed interoperability between computers using different operating systems, hardware platforms, and applications suites. Within the Government and industry these data transfer protocols, mostly oriented towards transmission and/or sharing of images and documents, have substantially improved the usefulness of office and home computers. With respect to medical instrumentation, however, such support for multiple platforms or distributed, object-oriented collection and analysis architectures for multiple data types do not yet exist.

To review relevant patent literature, U.S. Pat. No. 4,838,275 describes a home medical surveillance system which is designed to serve multiple patients in their homes. The system suggests the sensing of multiple parameters for patient health assessment and which are sent to a central observation sight. The data transmission/reception methods described predate the widespread use of the modern, distributed Internet concepts, and instead rely on simple point-to-point data transfer without specific data-independent object-oriented encapsulation coding methods. Data interpretation is strictly manually performed by a human observer, with no means for automated signal interpretation, and there is no indication that the input channels for data are in any sense general purpose.

U.S. Pat. No. 5,228,450 describes apparatus for ambulatory physiological monitoring which includes compact portable computer controlled data acquisition of ECG signals, including buffering and display. The invention focuses on the collection of ECG data and does not describe how any other physiological signal might be acquired. Nor does the invention include a communications means or an architecture in support of propagation encapsulated object-oriented data.

U.S. Pat. No. 5,231,990 describes an applications-specific integrated circuit for physiological monitoring which supports multiple inputs to implement flexible multi-channel medical instrumentation. The signal processing and programmable gain functions described are consistent with ECG-type filtering and monitoring. However, the subject matter does not involve communications or network interoperation, data buffering, data encapsulation, or an architecture for routing, buffering, and analysis. While the invention does involve programmable functions, it does not describe how it could be applicable to all relevant medical signals (specifically EEG).

U.S. Pat. No. 5,331,549 describes a medical monitoring system which supports a plurality of vital signs measurements supplied on a continuous basis to a central data collection server, which in turn, provides various display functions. The invention does not indicate that the vital signs inputs are multiple function, that the central computer is networked to other systems so that data collection and viewing can occur anywhere in the network, or that data is in anyway encapsulated for object-oriented processing.

U.S. Pat. No. 5,375,604 describes a transportable modular patient monitor which supports the collection of data from a plurality of sensors. The system supports multiple types of data through attachable applications-specific pods which have the electrical characteristics necessary to match specific low-gain sensor input signals (EKG, blood pressure, pulse oximetry, etc., but not EEG). The system transfers data to and from the patient and display systems through a local area network connection. Key innovations appear to be modular signal specific data collection pods, detached portable monitoring system with docking stations, and a means for providing continuous monitoring. The patent does not describe input channels which, under programmed control, are configurable to all medical sensor inputs, nor does it describe a local and wide area network data collection, encapsulation, routing, or analysis.

U.S. Pat. No. 5,458,123 measures vital signs sensors and uses a multiple antenna-based radio direction finding system for tracking patient location. The system is restricted to low-gain physiological signals such as EKG, temperature, heart rate, etc.

U.S. Pat. No. 5,438,607 describes a programmable monitoring system and method for use in the home, medical ward, office, or other localized area. A particular pulse-coded RF signal coding system transmits calls for emergency service to a home/office receiver which, in turn, is routed through telephone network to a central monitoring office. The invention involves wireless transmission and routing from a single point to point, but does not involve collection of physiological data, nor the transmission, buffering, or analysis of such information.

U.S. Pat. No. 5,549,117 describes a system for monitoring and reporting medical measurements which collect data on a remote stand-alone monitoring system into a relational database. The remote unit provides a means for generating reports and transmitting them to a health care provider. The disclosure is principally directed toward respiratory function sensors.

U.S. Pat. No. 5,558,638 describes a system for monitoring the health and medical requirements of a plurality of patients using a base unit located at each patient to connect to a number of sensors and/or recorders. The base unit stores the data which is transferred to a care center which analyses the data. The care center can also communicate with the base unit through a local area network. No evidence is given for hardware support for EEG or other vital signs measurements from a general purposed programmable analog input system, nor is a method for data encapsulation described.

U.S. Pat. No. 5,590,648 describes a personal heath care system which supports a plurality of patient monitoring sensor modules, but does not support multi-function analog inputs. A data processor with data communications modem is described, but not a wide/local area network connections coupled to a distributed encapsulated data collection, buffering, routing, and analysis system. Means are not provided enabling one or multiple patients to be monitored by one of many monitoring stations.

SUMMARY OF THE INVENTION

The subject invention satisfies the need for a general-purpose, low-cost system which provides comprehensive physiological data collection, with extensive data object oriented programmability and configurability for a variety of medical as well as other analog data collection applications. In a preferred embodiment, programmable input signal acquisition and processing circuits are used so that virtually any analog and/or medical signal can be digitized from a common point of contact to a plurality of sensors. A general-purpose data routing and encapsulation architecture supports input tagging and standarized routing through modern packet switch networks, including the Internet; from one of multiple points of origin or patients, to one or multiple points of data analysis for physician review. The preferred architecture further supports multiple-site data buffering for redundancy and reliability, and real-time data collection, routing, and viewing (or slower than real-time processes when communications infrastructure is slower than the data collection rate). Routing and viewing stations allow for the insertion of automated analysis routines to aid in data encoding, analysis, viewing, and diagnosis.

DETAILED DESCRIPTION OF THE INVENTION

The present invention relates to medical instrumentation and a methodology for use involving object-oriented measurement, collection, communication, and analysis. In terms of physical configuration, the apparatus is preferably in the form of a small, portable/wearable system supporting programmable measurement of multiple physiological signals from a plurality of sensor types, attached via remote collection, communications, and networking capabilities, to systems which support signal and signal feature analysis and interpretation.

Broadly, and in general terms, important features of the invention include:

(1) All data are read through programmable multi-sensor analog input processing stages, which are software configurable for signals ranging from very small signal EEG to very large signal volume or blood pressure sensors;

(2) All data are time and source tagged for integration into the spatial/temporal reality;

(3) All data are either self-descriptive, or encapsulated and object-oriented, so that at any point in the network any software system can acquire data by specific temporal/spatial or content features, and can understand the basic structure of the data items (i.e. data types). This facilitates standardized processing functions for specific data types which are available on each processing platform or collection/buffering/routing site, and further allows for extending these built-in functions through applications specific codes associated with specific data/record types. For ease of functional extension, a heterogeneous programming language environment and operating system environment is supported through use of standard program and data description languages;

(4) All data is transmitted and buffered to ensure delivery from input point to all processing/output points;

(5) Standard networking models support any reasonable network topology (i.e. support any number of patient collection modules delivering data to any number of patient data viewing/analysis stations), and exploit all relevant hardware network implementation standards (ranging from FDDI to RF/Wireless, satellite to land fixed). The network substructure must support geographic distribution of data sources and sinks (i.e. both wide-area and local-area networks); and (6) The standards underlying the system are based on public standards and language coding methods for computing system and operating systems independence.

Figure 1:
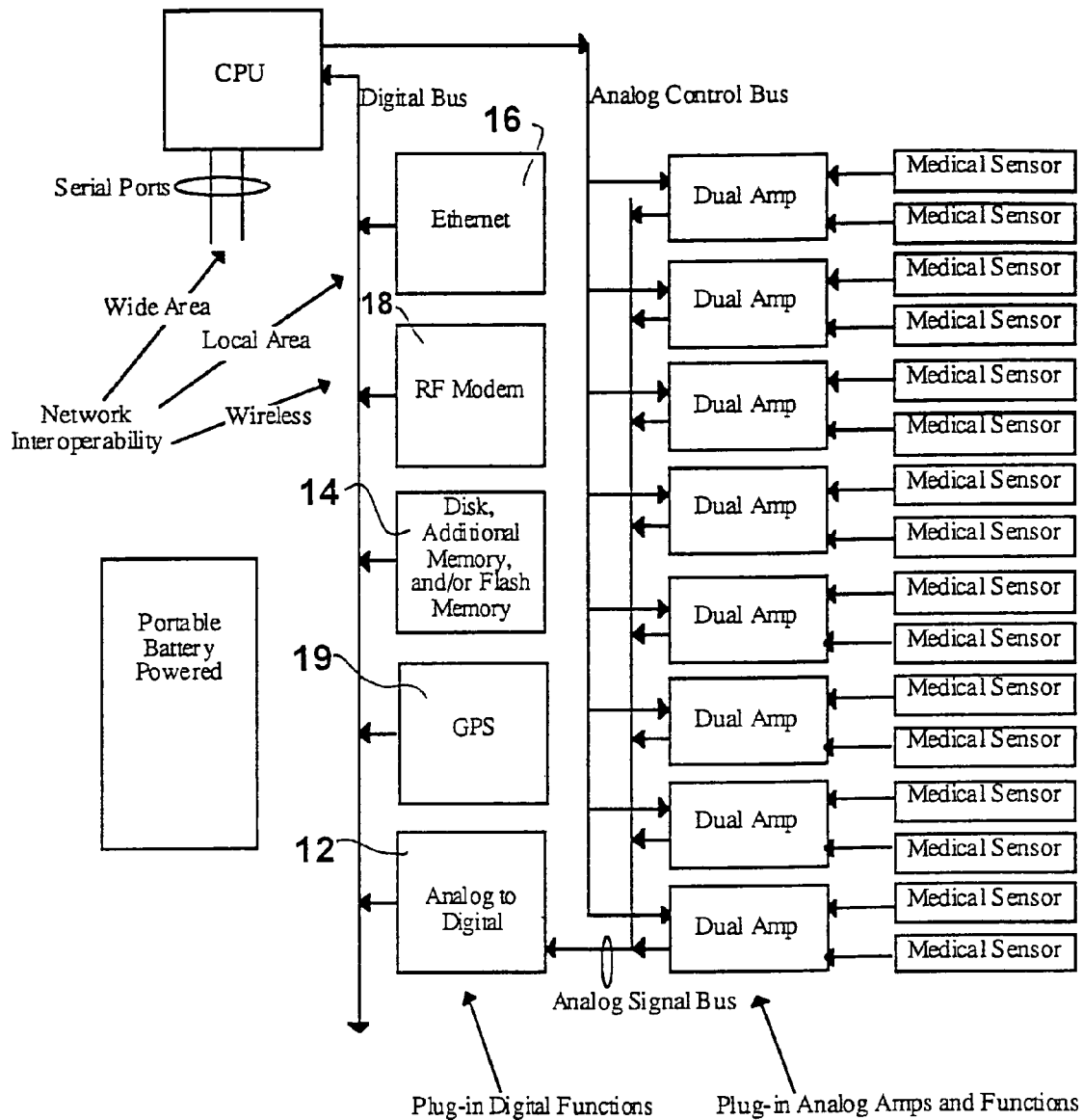
FIG. 1 is a drawing of a single portable/wearable medical instrument according to the invention.

A drawing of a single portable/wearable device according to the invention is illustrated in FIG. 1. The device is a comprehensive data collection system, capable of capturing multiple channels of physiological data from a variety of different sensor types. This functionality is achieved through a highly programmable design that allows for adaptation of each channel to any sensor type. The designed system allows for remote operability through its small (portable/wearable) size, long-term battery operation, high capacity data storage, and wireless or wired networking capabilities.

The device preferably uses a PCM/CIA interface for customization of system features through the use of standard PC-card modules. These PC-card modules may include:

Analog-to-digital converter (12) for sampling processed analog signals;

Data storage (14) in the form of a hard drive, flash RAM, and so forth;

Communications via Ethernet (16), modem (18), wired, wireless, etc; and

Optional features such as GPS location unit (19).

In addition, the system defines a standard ISA derived digital bus which is augmented by inclusion of a standard analog bus which supports multiple precision, programmable, variable-gain, variable filtering analog preamplifier/isolation amplifier stage cards. One benefit of PC-cards is that both the designer and the user can choose the means of communication between a remotely-used device and separated monitoring workstation (wireless or wired network communications), as well as the method of data storage (hard-disk drive or flash memory). In addition, data recorded over a 24-hour period and stored in the remote device can be transferred instantly to an analysis system containing a compatible PC-card slot, eliminating potentially long upload times.

The preferred implementation is based on an X86 CPU for its universal compatibility, however any appropriate CPU architecture may be employed. A modular design allows for use of different CPU boards to optimize the tradeoff between power consumption and computational requirements for a given application. For instance, for applications where additional processing power is desired a 486 processor can be substituted for a 386 processor, with no other hardware modifications required.

Software is used to support communications with other devices using TCP/IP protocol over a variety of different hardware media, including RS-232, ethernet, wireless modem, etc. This feature allows for simultaneous, real-time monitoring of multiple remote monitoring systems from one or more workstation or portable computer. Additional inventive software running on each workstation provides for both the display and analysis of features for real-time and post-acquisition evaluation of measured physiological signals, as depicted in FIG. 2. Additional details are provided below with respect to the software infrastructure according to the invention.

The configurable and programmable nature of the system allows for the adaptation of any channel to a variety of sensors for measuring signals including: ECG, EMG, EEG, EOG, respiration, blood pressure, oximetry, and many other physiological signals and measurements. Compatible sensors include standard surface electrodes, active electrodes, strain gauges, pressure transducers, outputs from sensor modules such as oximetry or non-invasive blood pressure, and virtually any other applicable sensor type.

Figure 3:
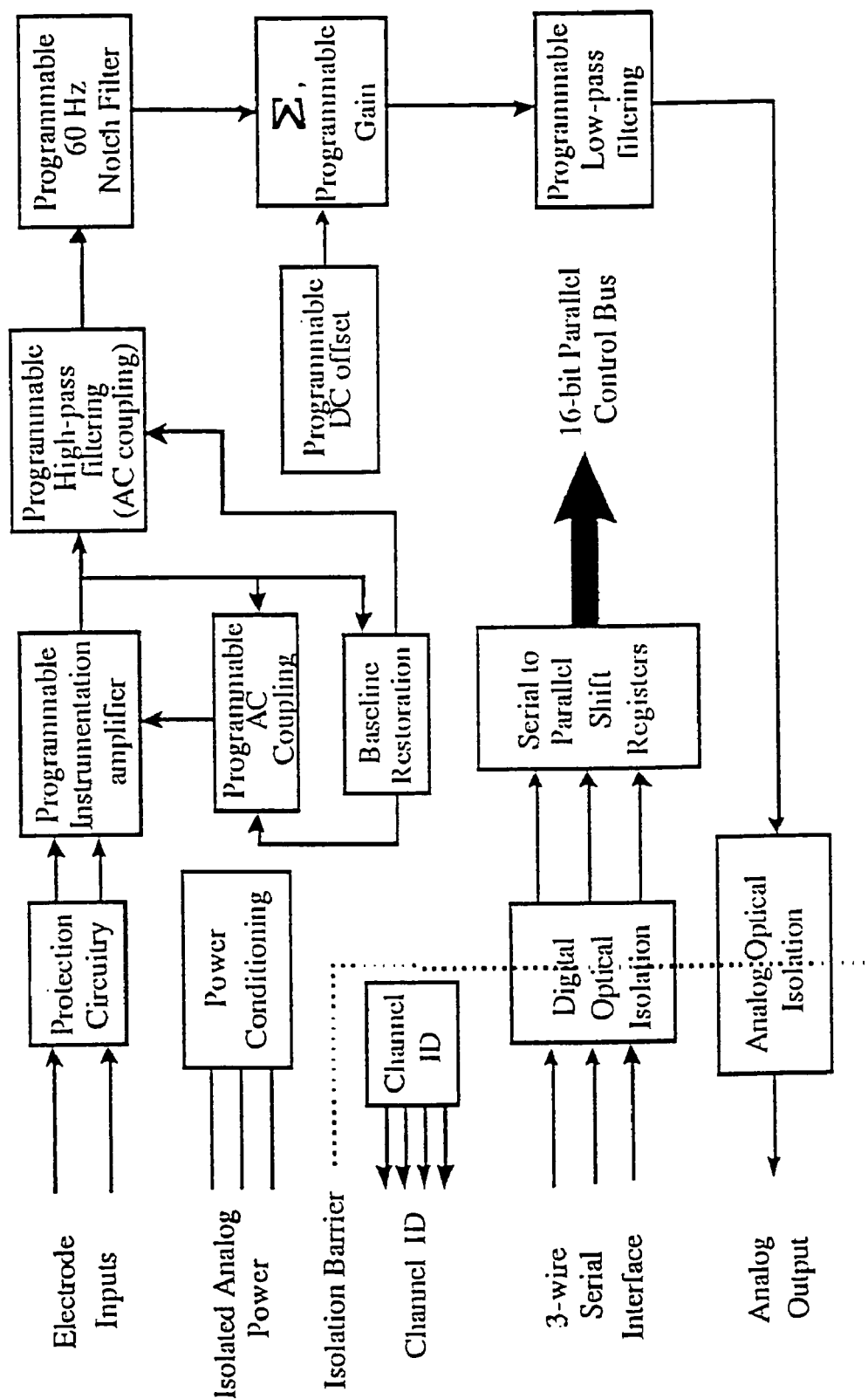
FIG. 3 is a block diagram of a programmable amplifier according to a preferred embodiment of the invention.

One means for achieving the highly programmable nature of the apparatus is through the incorporation of an inventive differential amplifier and signal conditioning circuit that provides extensive programmability through digital control lines. FIG. 3 is a block diagram of the programmable amplifier circuitry, and the following list summarizes the primary features of the amplifier design:

Microprocessor-compatible, optically isolated, 3-wire serial interface;

Optically-isolated analog output voltage;

Board-level power supply conditioning;

Less than 1 µV RMS equivalent input noise (gain>1000);

Wide input voltage range (+/−5 V);

Gain programmable from 1 to 300,000;

AC/DC coupling programmable with four highpass cutoff frequencies;

Programmable baseline restoration following saturation;

60-Hz notch filter programmable;

4-pole low pass filter with eight programmable cutoff frequencies;

DC offset adjustment programmable; and

Patient and equipment protection through current limiting stages and shunting elements.

Figure 4:
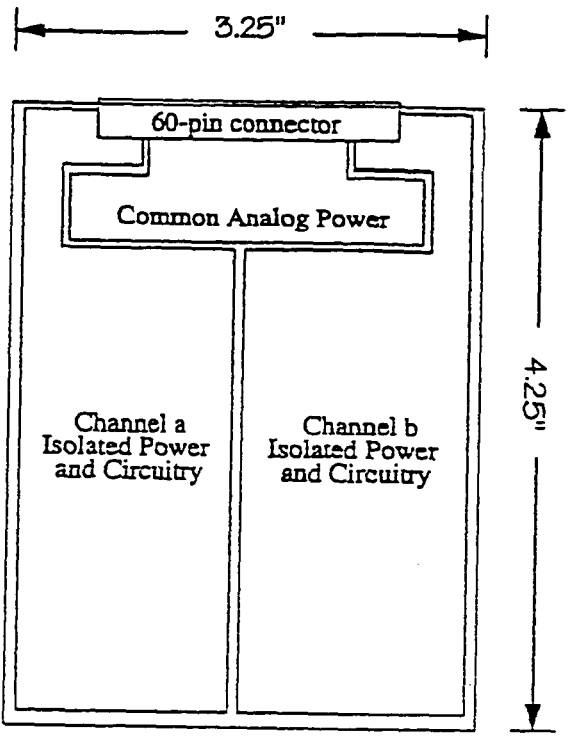
FIG. 4 illustrates a physical layout of one programmable amplifier board.

FIG. 4 illustrates a physical layout of one programmable amplifier board. Two programmable amplifier channels on a single PCB comprise a daughter-card which interfaces to a motherboard via a high-density connector. This connector supplies an input signal, isolated power, and a programming bit to each isolated amplifier channel, as well as to the two remaining common serial interface lines and a common power supply. The common serial interface lines are optically isolated twice on the amplifier board, once for each isolated amplifier channel, and supplied to each channel in addition to its respective isolated programming bit to yield the isolated 3-wire serial interface. The common power supply provides power to the output stages of the analog optical isolation stages of each channel. Additionally, the isolated analog output signals are carried from the amplifier board to the motherboard.

The system in which the amplifier card is used is not only designed to accommodate a programmable amplifier board, but a variety of other auxiliary function boards, including but not limited to pulse oximetry, noninvasive blood pressure, impedance respiration, or any combination of these functions. Data can be supplied to the system not only in analog form, as is done for the amplifier cards, but also digitally using the two available RS-232 ports which are accessible to a card inserted into the appropriate position (for non-PC implementations other digital ports can be included in the design concept). Therefore, nearly any control or acquisition function can be accomplished using these two interface types.

Digital Optical Isolation

Digital optical isolation of each of the 3-wire serial interfaces for each amplifier channel is performed on the amplifier board, preferably through the use of NEC high isolation voltage photocouplers (PS2801-4) having a high 2.5 kV isolation voltage.

Microprocessor Interface: Serial to Parallel Shift Registers

The programmable amplifier board receives its control via a microprocessor compatible 3-wire serial interface. This interface includes a clock line, a data line, and a programming line. Both of the amplifier channels on a given amplifier card share the same clock and data lines, but have individual programming lines. The serial interface drives a pair of serial input, parallel output 8-bit shift registers which generate the 16-bit programmable data bus for the given amplifier channel. The 16 data bits are clocked on the data line with the programming bit asserted low. Following the 16 data bits, on the rising edge of the programming bit the 16 data bits are latched onto the parallel data bus.

Protection Circuitry

Patient protection consists of a series current-limiting resistance which limits the fault-mode patient leakage current to 30 uA via the electrode interface. Under normal operation, the patient leakage current via the electrode interface is limited to the leakage current of the isolated supply circuitry (pA), the leakage current of the input filtering capacitance (pA), and the leakage current of the instrumentation amplifier (pA).

Amplifier protection consists of a pair of fast-switching diodes tied to the supply rails which will limit the voltage at the input of the differential amplifier to the supply rail voltage plus approximately 0.7 V. This protection, combined with the 0.1 W series current-limiting resistance is capable of protecting the input of the amplifier from exposure to 110V, 60 Hz line supply. Additional amplifier protection can be implemented on the motherboard to allow for protection from high voltage, high-power transients such as a defibrillator pulse.

Programmable Instrumentation Amplifier

The differential input signal supplied to each amplifier channel is amplified by a programmable instrumentation amplifier, the Burr-Brown PGA204, with programmable gains of 1, 10, 100, and 1000. This amplifier combines a high input impedance, low input noise, high common-mode rejection ratio (CMRR), and programmable gain in a single package. The gain of the instrumentation amplifier is selected by data bits 0 and 1 of the parallel data bus.

Programmable AC Coupling

In many cases it is necessary to remove the DC component of an input signal, particularly when employing high system gain. The remaining portion of the AC coupled signal can then be amplified further without saturation of the output due to a DC component which is often of much greater magnitude than the AC signal of interest. In order to most effectively reduce the DC component of the signal, an integrator is placed in a feedback loop between the output of the instrumentation amplifier and its reference. Thus, any DC component of the input is effectively subtracted from the output of the instrumentation amplifier. To allow for flexible use of this amplifier, this AC coupling feature is programmable, with choices of DC coupling or AC coupling using one of four selectable cutoff frequencies. These cutoff frequencies are shown in Table 1. For DC coupling, the integrator is removed from the feedback loop by an analog switch which then supplies a buffered ground signal to the reference pin of the instrumentation amplifier. AC or DC coupling are selected using bit 5 of the parallel data bus, while the AC cutoff frequencies are selected by bits 2 and 3.

TABLE 1

| Feature 1 | Description |
| --- | --- |
| AC/DC Coupling | Programmable with 4 cutoff options (programmable): |
| | 0.01 Hz |
| | 0.1 Hz |
| | 0.5 Hz |
| | 20 Hz |
| Highpass Filter | 4-pole HPF, with 4 cutoff options (programmable): |
| | 0.01 Hz |
| | 0.1 Hz |
| | 0.5 Hz |
| | 20 Hz |
| 60 Hz Notch Filter | Programmable in/out |
| Lowpass Filter | 4-pole LPF, with 8 cutoff options (programmable): |
| | 20 Hz |
| | 50 Hz |
| | 100 Hz |
| | 200 Hz |
| | 500 Hz |
| | 1000 Hz |
| | 5000 Hz |
| | 10000 Hz |
| DC offset adjustment | Programmable: |
| | −4.1 to +4.1 volts |
| Gain | Programmable: |
| | 1 to 300,000 with 10 increments per decade |
| Power system | Individually isolated channels |

TABLE 1-continued

| Feature 1 | Description |
| --- | --- |
| CMRR | 120 dB @ 10 Hz |
| | 107 dB @ 100 Hz |
| | 87 dB @ 1 kHz |
| Noise Level | <1 uV RMS |
| User Protection | Current limiting (30 uA) |

Programmable Baseline Restoration

When using the lower AC coupling or highpass filter cutoff frequencies and the amplifier saturates due to a large input, the output takes a great deal of time to return to baseline due to the long time constants of the integrator and highpass filter. In many instances this behavior is not tolerable due to the loss of potentially valuable data. In order to restore the output of the amplifier channel to its correct value following saturation, a baseline restoration circuit has been incorporated which takes advantage of the programmability of the AC coupling and highpass filter cutoff frequencies. The output of the instrumentation amplifier is buffered then passed through a full-wave rectifier. The output of the rectifier is compared to a reference voltage representing amplifier saturation. When saturation is detected, the comparator output goes from a logical low to a logical high, which, if baseline restoration is enabled, switches the integrator and highpass filter cutoffs to their highest setting. This provides the quickest return of the signal from its saturated state to its correct output, at which time the cutoffs are restored to their programmed value. This baseline restoration feature is controlled by data bit 15 of the parallel data bus.

Programmable Highpass Filter

A 4-pole highpass filter has been implemented based upon a unity-gain voltage-controlled-voltage-source (VCVS) analog filter. The four cutoff frequencies are selected using differential analog multiplexers controlled by data bus bits 2 and 3 to simultaneously switch between the cutoff-selection resistors of each of the two stages of the VCVS filter.

Programmable 60 Hz Notch Filter

A programmable 60-Hz notch filter has been implemented using a bootstrapped twin-T configuration. The notch frequency of the filter is fixed by the choice of component values, while the notch depth is configurable as either 0 dB (notch filter "out") or approximately 30 dB (notch filter "in") by the selection either a high or low valued feedback resistance via an analog switch controlled by bit 7.

Programmable DC Offset

A programmable DC offset signal is derived from a precision voltage reference, whose output is 4.1V. Additionally, this output is inverted via an inverting amplifier and precision 0.1% tolerance resistors to yield 4.1V. These two voltages are tied to the end terminals of a Dallas Semiconductor digital potentiometer having 256 positions, the wiper of which determines the DC offset. When the wiper is centered, the DC offset is 0 V. Advancing the wiper position towards the positive reference voltage results in a positive DC offset ranging from 0 to 4.1V, while advancing the wiper position towards the negative reference voltage results in a positive DC offset ranging from 0 to −4.1V. Thus, combined with the instrumentation amplifier gain of up to 1000, as small as 16 mV may be referred to the input. The offset is controlled via the 3-wire serial interface of the digital potentiometer, which is comprised of bits 8, 9, and 10 of the parallel data bus.

Programmable Gain

The resulting DC offset is then added to the amplified input signal via an inverting summing amplifier having a selectable gain of 1 or 10 as determined by parallel data bit 6. This programmable gain is accomplished using a SPDT switch to select the feedback resistor of the summing amplifier to set a feedback-to-input resistance ratio of either 1 or 10.

A third stage of programmable gain is implemented using a Dallas Semiconductor digital potentiometer in an inverting amplifier configuration. The wiper is connected to the inverting terminal of the op amp to keep wiper current to a minimum. The gain is set by the ratio of the two terminal-to-wiper resistances, thus providing a temperature-stable and terminal resistance-independent gain stage with gains ranging from 0 to 255. The digital potentiometer is controlled via its own 3-wire serial interface, which is comprised of bits 8, 9, and 10 of the parallel data bus.

Programmable Lowpass Filter

A 4-pole lowpass filter has been implemented based upon a unity-gain voltage-controlled-voltage-source (VCVS) analog filter. The eight cutoff frequencies are selected using analog multiplexers controlled by data bus 11, 12 and 13 to simultaneously switch between the cutoff-selection resistors of the VCVS filter.

Analog Optical Isolation

Analog optical isolation has been implemented using a linear isolation amplifier design based on the LOC series of CP Clare linear optocoupler devices to provide 3750 VRMS isolation. The amplifier is configured in photovoltaic operation to enable the highest linearity, lowest noise, and lowest drift performance. The linearity in this mode is comparable to a 14-bit D/A with a bandwidth of about 40 kHz. The LED of the optocoupler is driven with a transistor buffer to maintain the highest linearity and to minimize total harmonic distortion (THD). A +/−2.5V bipolar input signal is offset by the bias resistor in the servo feedback path to create a 0-5V unipolar signal which is passed over the optical barrier and used as the output of the amplifier module.

Channel ID

Each card channel carries its own 4-bit tri-state buffer so that all 16 channels may share the same common data channel ID bus. When a given channel is "queried," i.e. its select line is asserted low, the channel places its ID on the bus, allowing the system software to determine the way in which the unit is configured. The channel ID of an amplifier channel has been set to the 4-bit ID 0001. When no card is in place, the default channel ID is 1111 which, if both channel IDs for a given slot correspond to this value, the system software interprets as a vacant card slot.

In addition to measurement of data through circuitry on internal data cards, a serial data link can also be established with an external device, such as pulse oximeter, blood pressure monitor, $CO_2$ monitor, etc. This allows for simultaneous collection, time-stamping, and collection/transmission of all measured data, including that from separate devices. The system also includes a simple user interface, consisting of pushbuttons and a small graphic-capable liquid crystal display (LCD). This will allow for programmable interaction between the device and the user even during remote usage away from the linked workstation. This offers many significant opportunities for enhancing the functionality of a portable implementation of the invention, including:

device status indication (battery level, communication link status, etc.);
 display of measured signals and health status;
 biofeedback;
 system configuration/device setup; and
 event marking and categorization.

Figure 5:
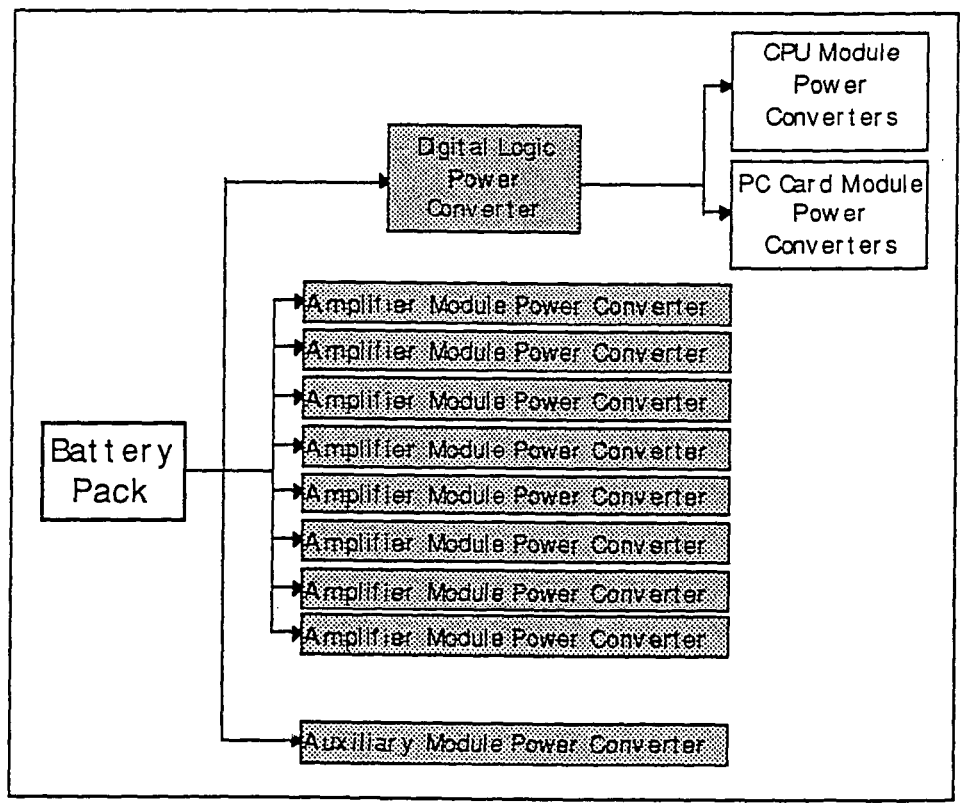
FIG. 5 is an illustration of a distributed power supply.

The user interface also allows for sampling of patient-supplied information and responses to questions (i.e. an electronic diary) during collection of physiological data, with time synchronization. The system preferably further includes a distributed power supply as shown in FIG. 5. This provides individually isolated power supplies to each of the amplifier/signal conditioning modules, to the auxiliary modules, and to the digital circuitry (CPU, PC Cards, LCD Display, and supporting logic).

In the preferred configuration, the digital logic power converter is located in an external "power module" which will be physically and electrically connected to the battery pack. All other power conversion components are located inside the unit. This arrangement allows for the development of different power modules optimized for particular battery chemistries and cell arrangements, as well as decreasing heat dissipation inside the device. For configurations which require extremely long-term data collection (i.e. for durations longer than the maximum that can be achieved with a single battery pack), the power module contains a small nickel-cadmium backup battery that will allow the main battery pack to be swapped without interrupting the data collection. This backup battery pack will be charged by the main pack during normal operation. The power module also contains circuitry to detect low battery voltage and to control main system power. This circuitry is optically interfaced to the CPU board to allow the software to monitor battery status and to control system shutdown.

The response to a detected low-battery condition is determined by the type of power module installed. If the power module does not support hot-swapping of battery packs (that is, if it lacks a backup battery), the software will close any pending data collections in an orderly manner and then shut down the system. If the system is configured with a power module that does contain a backup battery, a warning message will be displayed (and will also be sent to any remotely connected nodes) and a short-duration (1 to 5-minute) countdown timer will be initiated, giving the user a short time to replace the discharged battery pack while the system is being powered by the backup battery in the power module. If the main battery back is not replaced by the end of this time-out period, the system shutdown sequence proceeds as described above.

Once the system has been shut down (either due to a low-battery condition or by explicit software command), it will remain in a powered-down state until the main battery pack is disconnected from the power module and a new, adequately charged pack is connected.

Figure 6:
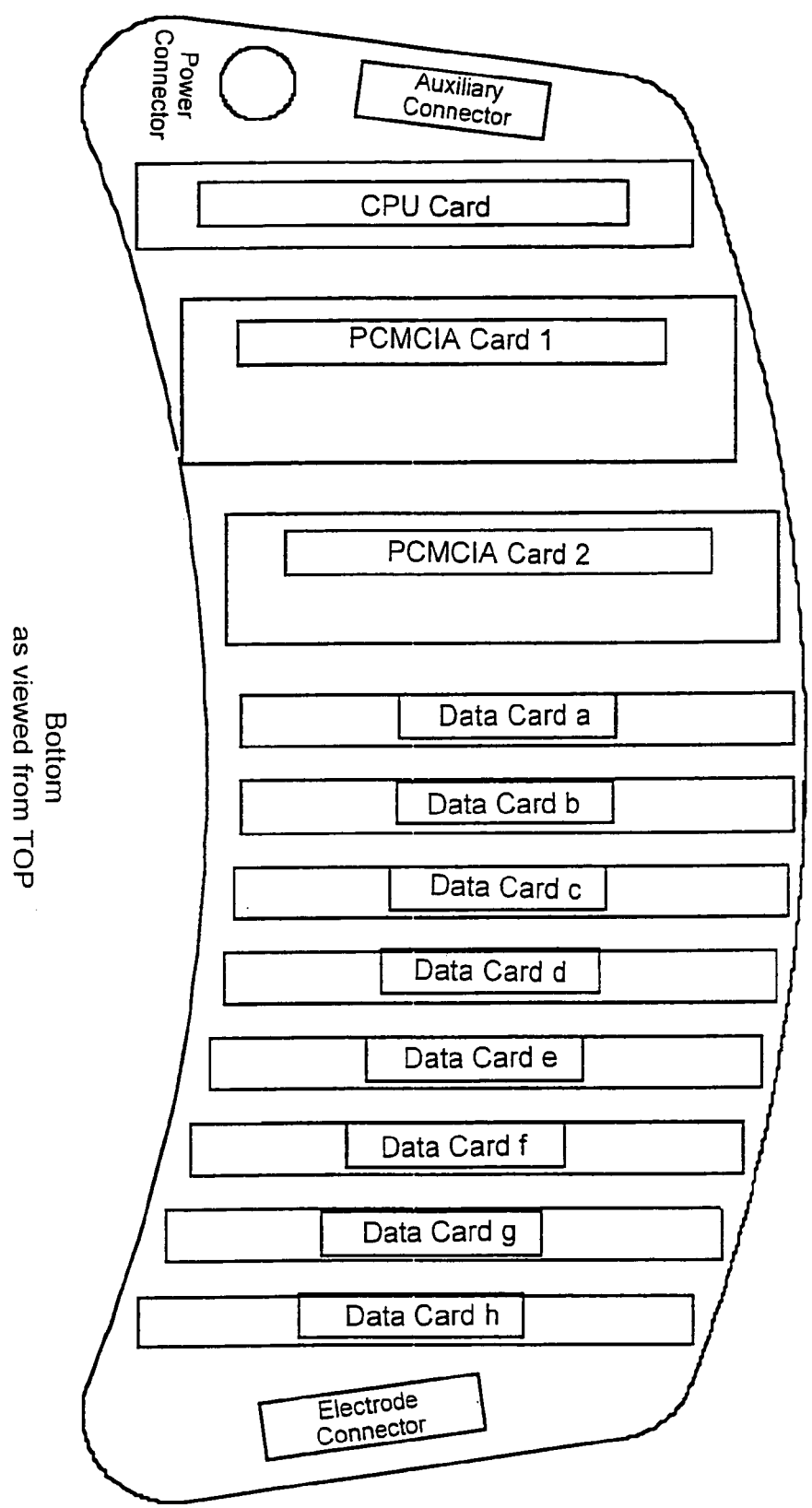
FIG. 6 illustrates a connection configuration between a mother board and daughter cards.

For effective packaging and interfacing of the electronics, the system is preferably divided into the following four distinct board types: motherboard/backplane; CPU controller board; PCMCIA carrier board; and datacard boards (AMP board and other custom sensor interface boards). The CPU, PCMCIA, and data card boards each interface to the Mother Board as daughter cards. FIG. 6 illustrates the connector configuration of the mother board, not drawn to scale.

Figure 7:
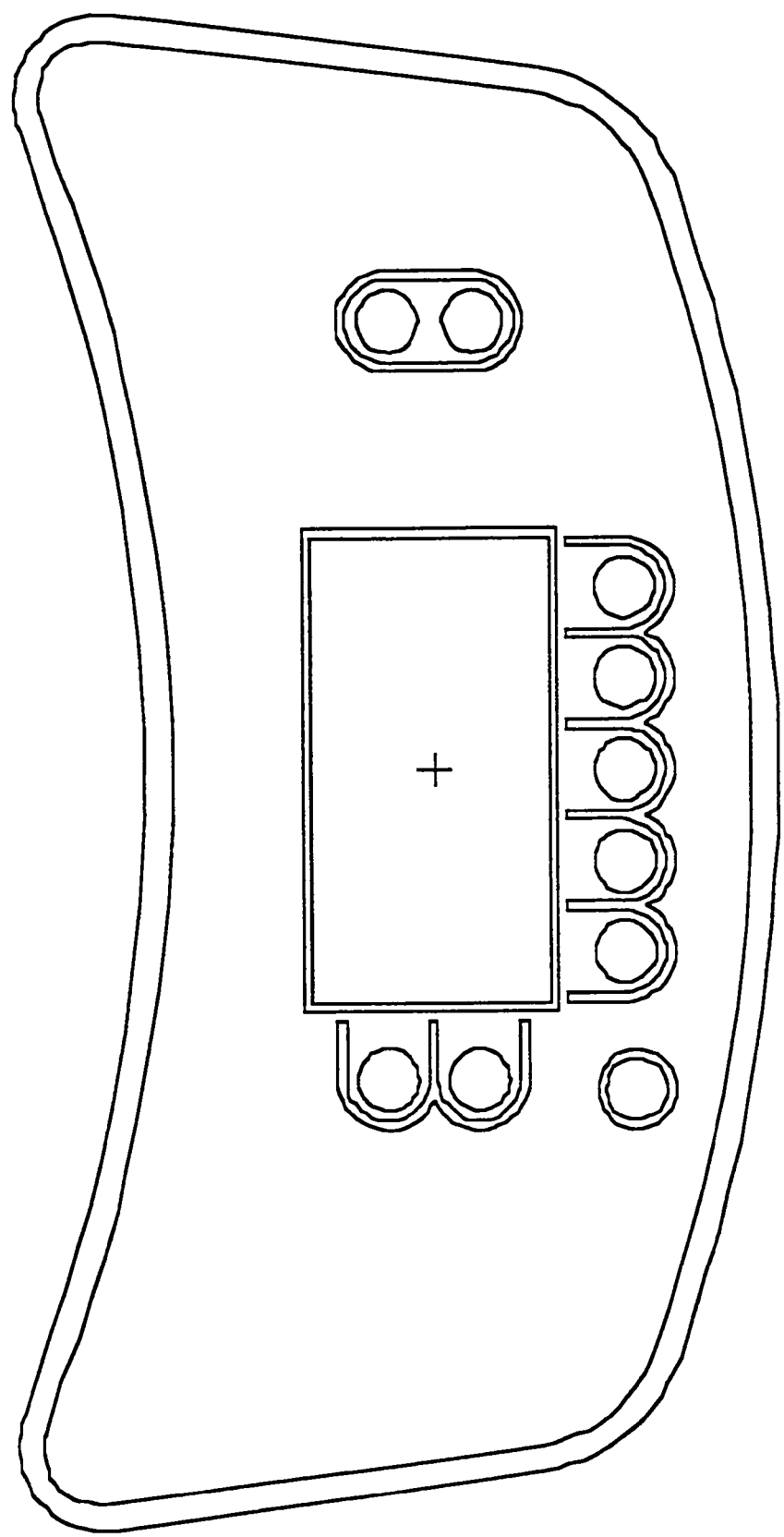
FIG. 7 is a drawing which shows a front display and switch panel.
Figure 8:
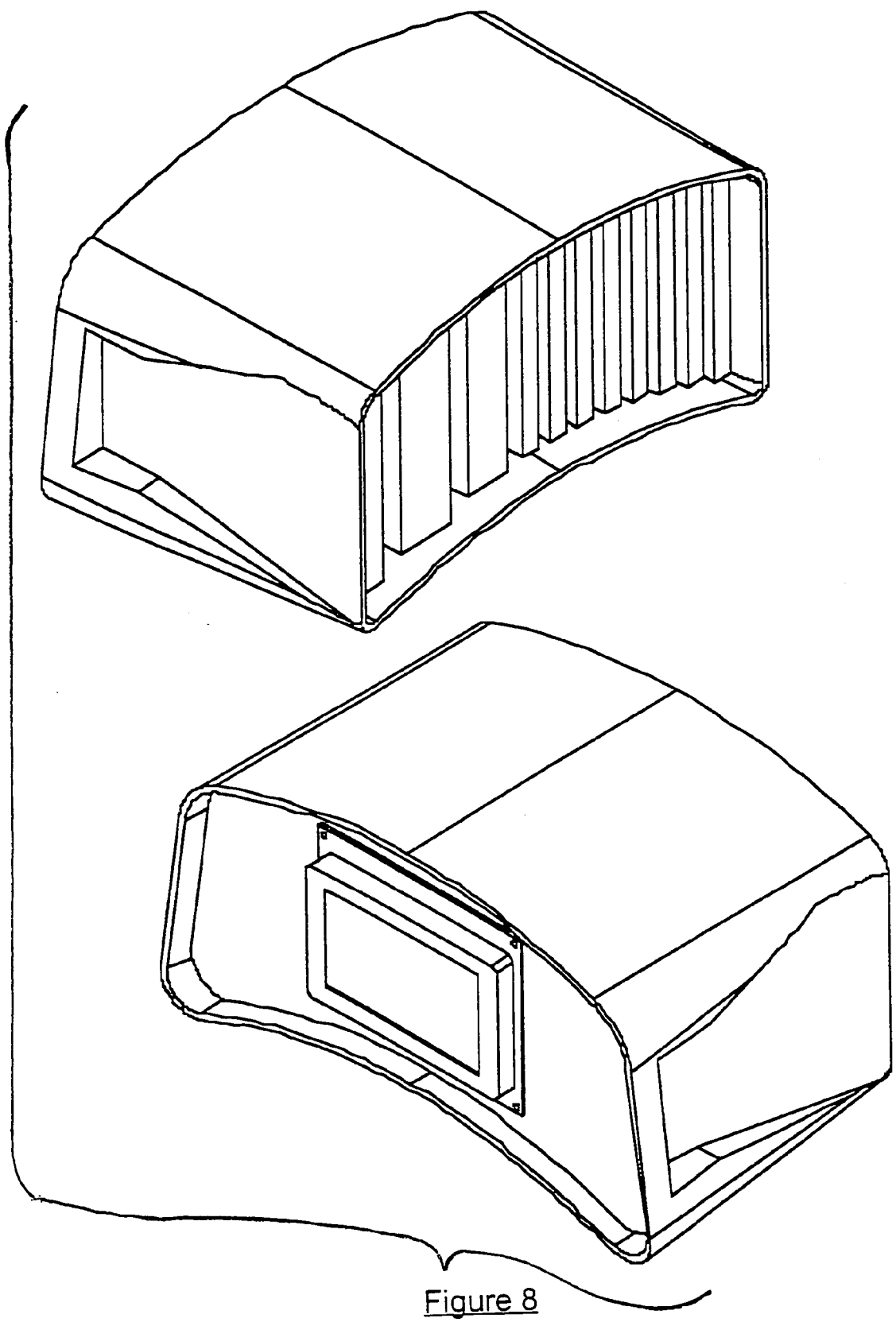
FIG. 8 provides two oblique views of a physical layout of a system according to the invention.
Figure 9:
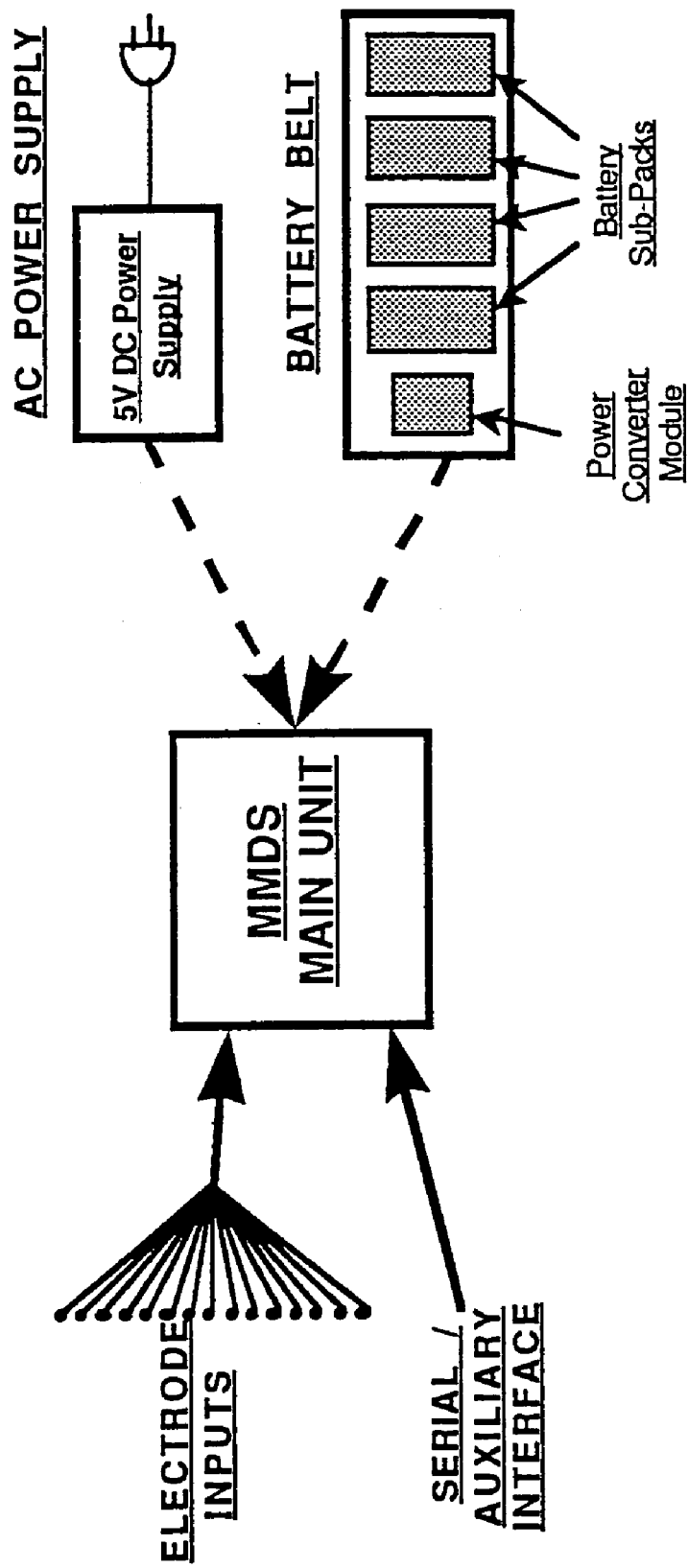
FIG. 9 is a block diagram of a portable portion of the inventive system.

Front display and switch panel of the MMDS collection device is illustrated in FIG. 7. It includes provisions for 16 amplifier inputs (or alternative analog devices), CPU, Display, Disk, and four PCMCIA devices (GPS, LAN, A/D, RF Modem). FIG. 8 shows the physical layout of the system, and FIG. 9 is the block diagram of the entire portable portion of the system.

Data Collection, Encapsulation, Routing, and Analysis Architecture

Figure 10:
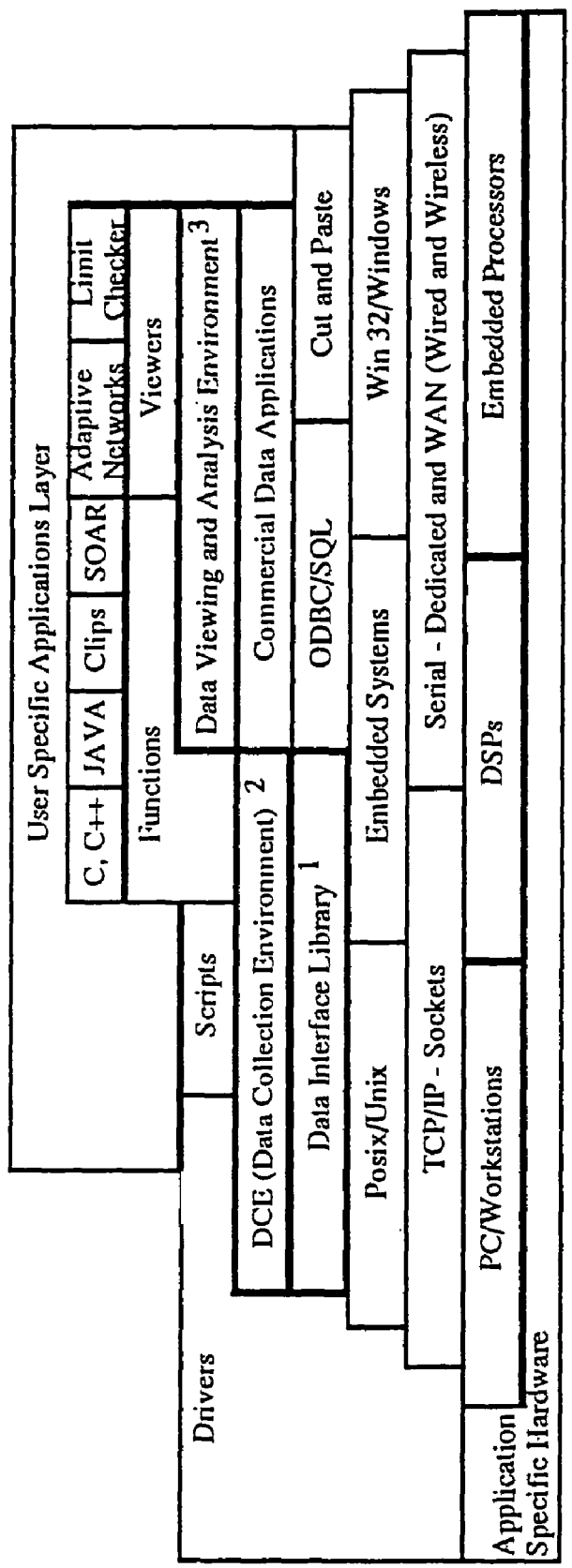
FIG. 10 illustrates how the invention provides a point of collection and digitization for multiple types of medical data.

The invention provides a point of collection and digitization for multiple types of medical data. The data is labeled, stored, and uploaded to a network at environment (DCE). This environment is structured into three major C++ software components: (1) the Data Interchange Library, (2) the Data Collection Environment, and the (3) Data Viewing, Analysis, and Management Environment. This environment, shown in FIG. 10, is supported on Win 32 platforms (i.e. Windows 95 and NT), Posix Platforms (i.e. Unix derivatives), and embedded system (DSPs, MS-DOS machines, and other microcontrollers). The system as currently configured supports data viewers, SQL/ODBC interfaces (to data intensive applications), AI plug-ins (CLIPS and SOAR), user plug-in functions written in multiple languages (JAVA, C, C++, Perl), and data capture subsystems (from sock/serial data/message sources, intelligent A/D-D/A subsystems, Unix/Win 32/embedded system operating systems event and network traffic measurement sources, GPS, Compass, and Head/Eye Trackers, digital video sources, and physiological data measurement sources).

Figure 11:
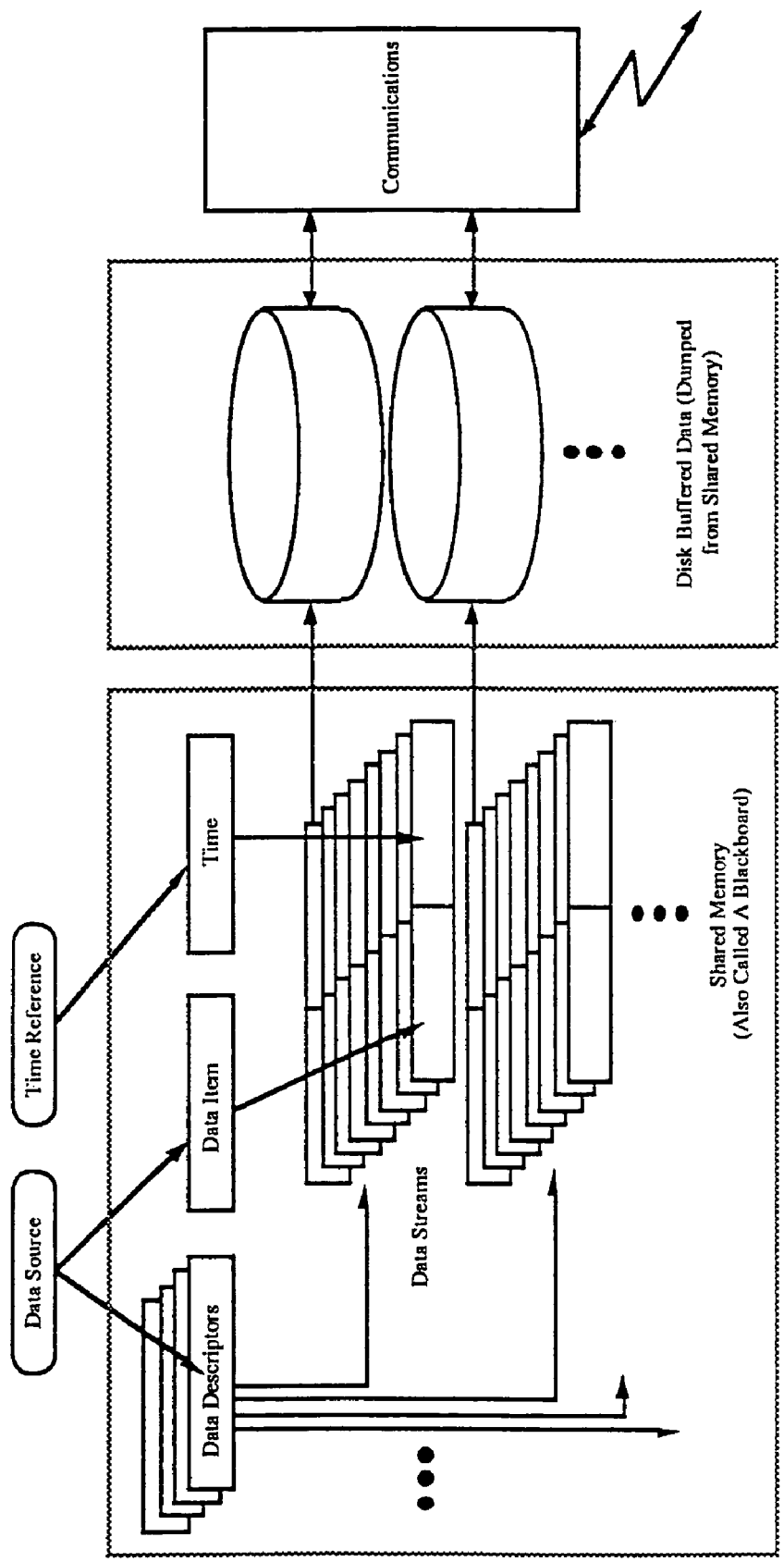
FIG. 11 illustrates how, according to the invention, an underlying architecture may be based upon standard data encapsulation.

The underlying architecture of the system is based on standardized data encapsulation (FIG. 11). Each data source produces data structures composed of tagged data items. Each data structure is implicitly or explicitly time stamped to the accuracy of the input systems time base (each input system is a particular computer on the data collection and management network). Each data management and input system synchronizes time through the best algorithms available ranging from use of GPS derived time to mutual synchronization over the interconnection network (through a sequence of timing data packet exchanges). Because a reliable time common base for data message tagging is inherent in the system, as data is buffered and flowed up and down the collection network, data order is well known at each point in the collection, databasing, and analysis functions of the overall system.

Through function plug-ins at each point of data buffering and management, users can add programmed functionality which initiates new data collection or output, monitors data streams as new data arrives, produces new views of the data, and/or works with precollected data either in temporal order or in arbitrary record field order (the later is supported through the SQL interface features in conjunction with an SQL compliant database system plug-in).

Figure 12:
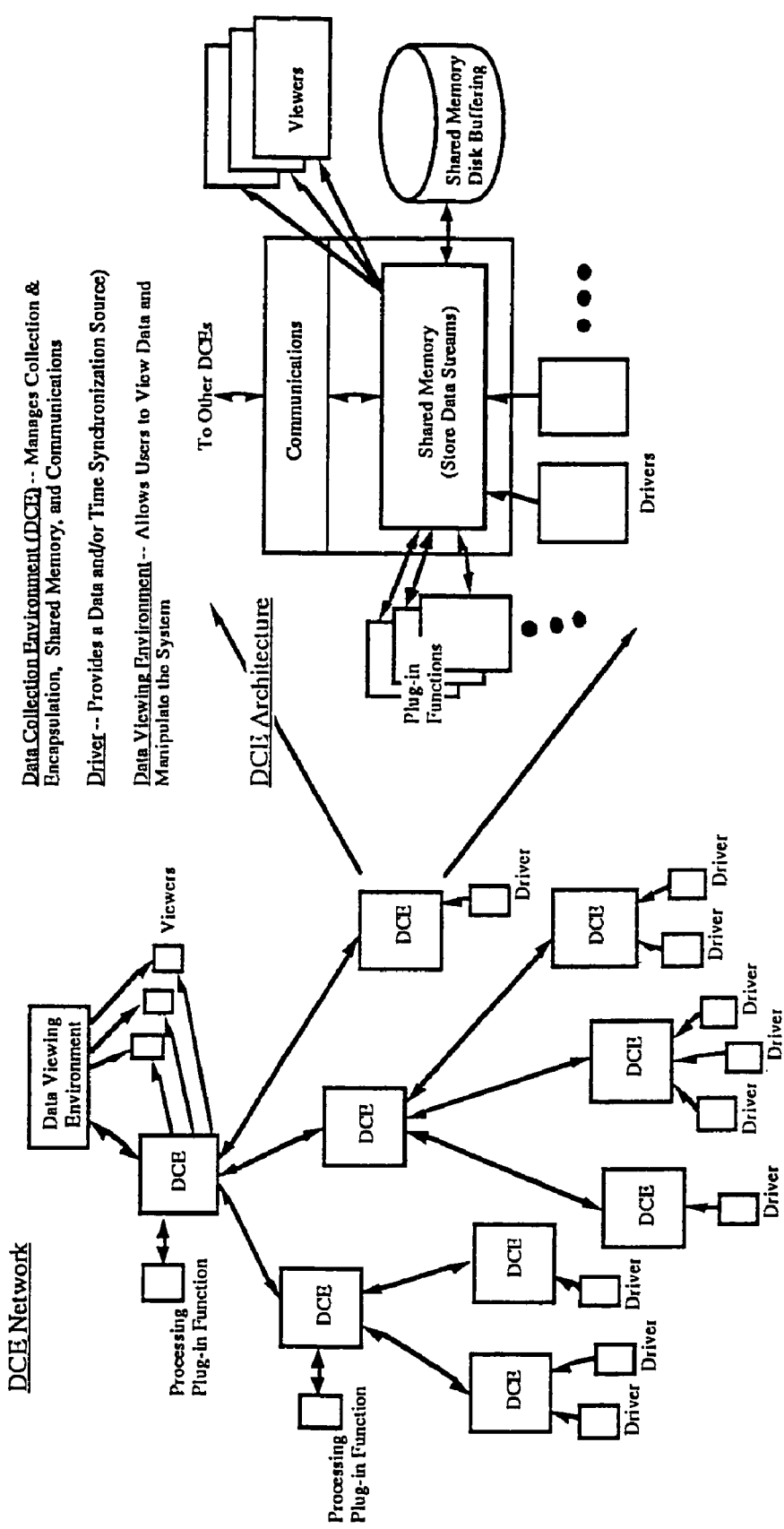
FIG. 12 is a drawing which shows the basic architecture of the invention as a hierarchy of collection-databasing nodes.

The basic architecture of the system is a hierarchy of collection-databasing nodes (FIG. 12), or data collection environments (DCEs). Each DCE node combines a data input subsystem, socket communications subsystem, a data caching shared memory (for object tags temporal data streams), and online disk-based buffering. Each node's communications subsystem can accept multiple streams from other sources (through socket connections) or from data input subsystems (A/D, serial, or other I/O ports). Each stream is encapsulated in the data input process (or at its data input source for data from the communication subsystems), and is stored in a shared memory interface as part of an established stream set. Each stream set, when established, support a defined data type, and relays the data stored to disk on specified intervals for permanent storage.

Through the Data Interface Library, the user can install functions or subtasks which attach to the shared memory and related functions through a set of standard C++ objects. This library allows an attached routine to instantiate data types or streams, enter new data items, retrieve items which are buffered (either in memory or on disk), instantiate data collection "drivers" and initialize/control them, and provide access to data on other node transparently, thereby making the entire data collection across multiple nodes transparently available to an application attached at any node.

Transparent data sharing between nodes is a feature of the DCE which is important in many test, measurement, and information fusion applications. DCE nodes on separate interconnection networks share each other's buffer and disk memory to provide virtual access to the totality of data available as input to the network. The notion of the distributed collection feature of the DCE is driven by two separate considerations. First, when performing critical, real-time collection, each physical computer will have a specific limited input bandwidth. Thus, to support potentially unlimited input bandwidth, the collection hardware must be replicated until sufficient hardware bandwidth is available for the requisite input signal array (FIG. 2A). By using accurate time bases for data fusion across the collection array, re-integration of the data is quite feasible (assuming the time base has better resolution than the signal events being captured).

Figure 2B:
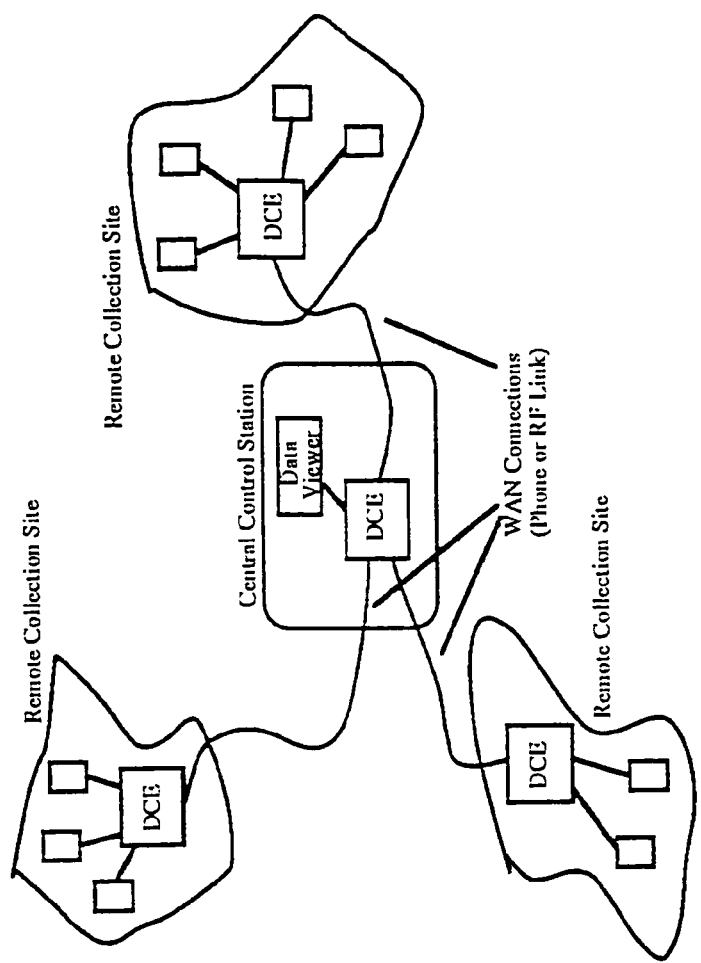
FIG. 2B illustrates how collection nodes may be physically separated to perform desired tasks.
Figure 2A:
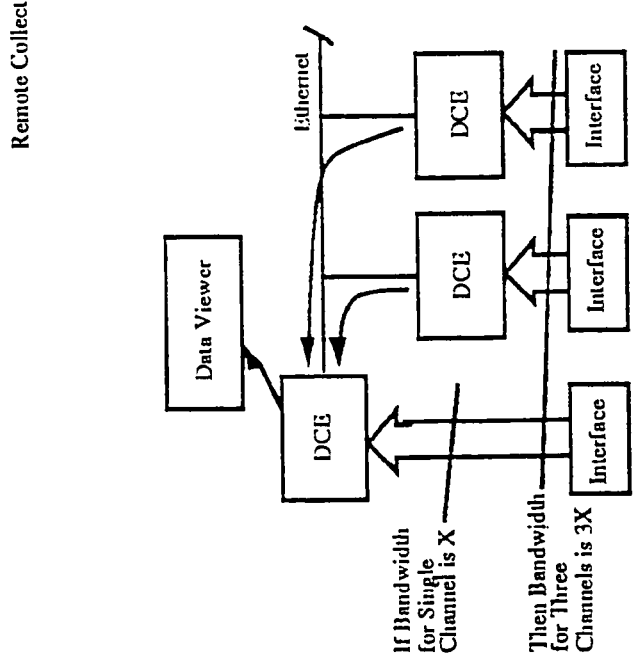
FIG. 2A is a drawing which shows how distributed collection may be used to support potentially unlimited input bandwidths.

Another reason for supporting distributed collection is that in some remote monitoring applications, the collection nodes must be physically separated to perform the desired tasks (FIG. 2B). As this separation distance becomes larger, maintaining control over the collection process and communications delays begin to make data integration impossible without an integrated accurate time base for data tagging. Also, communication bottlenecks make inherent data buffering a necessity, even when communications links are reliable and high in bandwidth.

As indicated previously, the DCE provides this buffering function as a combination of shared memory (i.e. RAM) and disk buffer. Thus, each node is capable of storing is own data collection locally, without direct transmission uplink to higher level nodes. Communications uplink is effected in one of two ways. First, some streams can be defined as having the property that they always stream data up to high level nodes. These streams "offer" data, usually for real time monitoring of the data collection process at the higher level node. Quite often, it is assumed at the higher level node that the data being send is "abridged" because of bandwidth limitations in the communications links. As such the upper level node knows that its datasets are only partially correct and thus, knows that if a function requiring complete information is executed, the data gaps must be filled in, perhaps at slower than real time rates. This abridged, or real-time data transfer mode is useful when monitoring the progress of testing or field operations, where maintaining real time situational awareness is more important than capturing, viewing, analyzing every data item (recall, that using the real time mode does not preclude reverting back to full data viewing later, because all the data collected is stored on its source node).

Figure 13:
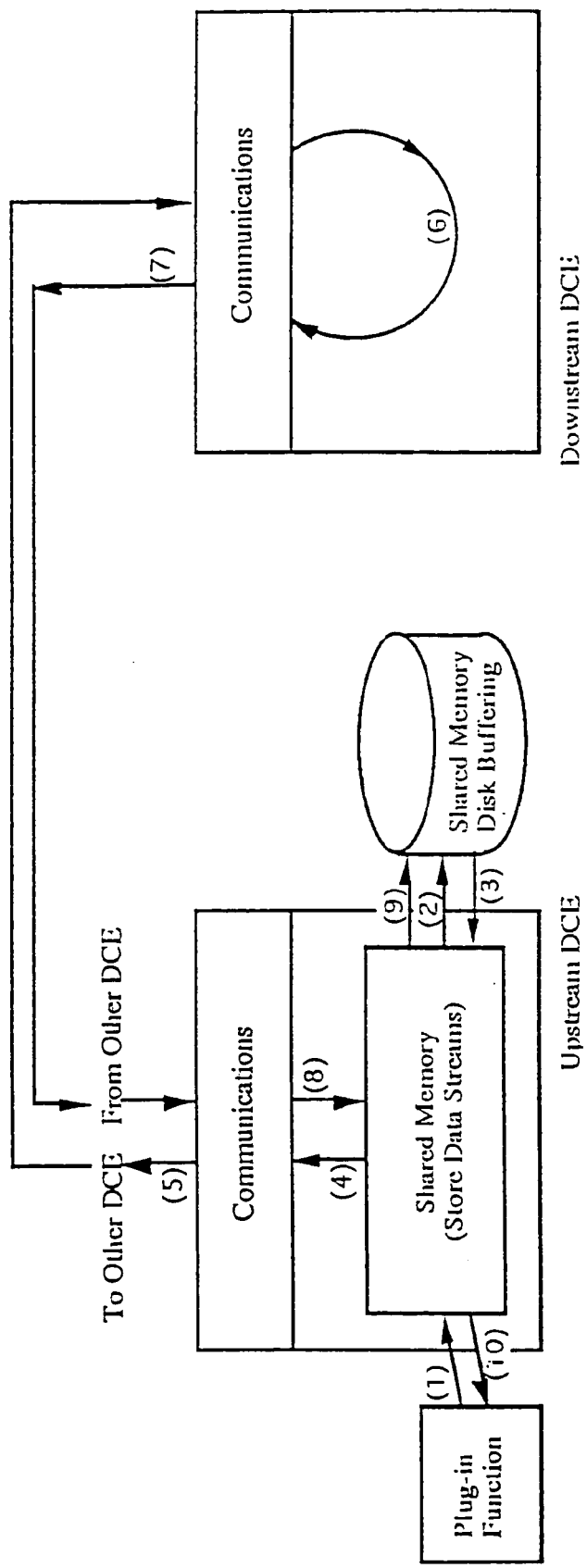
FIG. 13 illustrates how logic in a data interface library is used to connect a data source node to affect data upload on demand to complete a local data stream for a particular data request.

If an attached application requests data from a DCE buffering subsystem which is not locally present (i.e. data is either not being linked up from a lower level node or is being uplinked in real time mode with abridgment), logic in the Data Interface Library can connect to the data source node and can effect data upload on demand to complete the local data stream for the data request (FIG. 13). This capability makes all data for all collection and input nodes logically available on any DCE node for any attached function. Of course, this feature does not guarantee real time data availability unless the source node and the destination node are connected through communications links which are fast enough to hold up real time transfers. Since all data inputted is time stamped at its input source, data items are temporally consistent throughout the system so that data assimilated from multiple sources and uplinked at multiple times can still be consistently re-integrated.

The numerical references of FIG. 13 are defined as follows:
(1) DCE attached function requests a data stream segment;
(2) Shared memory is checked for the item and if fails to contain it proceed to (3), otherwise return item;
(3) Attached disk buffer indexes are checked and if fails to contain it proceed to (4), otherwise read item into shared memory and return it;

(4) Data Interface Library requests data item from connected DCE which sources data stream;
(5) Data request is converted to a socket or serial data request to the downstream DCE;
(6) The downstream DCE executes (2)-(4) and routes the item found to the upstream DCE;
(7) The item is returned to the requesting DCE through socket or serial communications;
(8) The data item is entered into Shared Memory;
(9) The item is saved in the disk buffer (whenever Shared Memory is saved periodically); and
(10) The item is returned to the requesting attached function.

As indicated previously, functions can be attached through the Data Interface Library, to any DCE node. Some of these functions are pre-compiled code (typically C or C++, but alternatively any other language which can support a C, C++ linkage). In Win 32 systems, precompiled functions are in the form of executables or DLLs. On Unix systems they are executables or share library routines. Examples of precompiled codes already provided for within the system are device drivers (routines which read data to or from hardware interfaces such as A/D-D/A ports, serial ports, video capture interfaces, etc.), data compression/decompression routines (includes data compression/decompression, data reformatting routines, and encryption/decryption routines), and heavy compute functions (such as data filters, FFT/DFT, spectrum analysis, etc.)

Some attached functions are interpreted or shelled functions, supporting languages like Perl, JAVA, or other CGI/Shell languages. These interpreted functions provide the user a means for implementing "throw away" functions quickly and easily. The function attachment method has also been used to implement a set of AI subsystems for pattern recognition, diagnostics, and model-based reasoning. These include CLIPS (a C-based expert system shell), SOAR (a more sophisticated expert system with learning), limit checking and decommutation (a simple indicator subsystem for satellite system diagnosis), and adaptive network processing (Neural Nets).

Device Drivers serve as initial points of entry for data into the system. The basic form of a driver is as an attached function. Each DCE has a command interface, similar to TELNET and FTP. This command interface allows a remote user to examine the suite of attached functions (including drivers) available at the node, supports adding and deletion of functions, data sets, and other configuration files, and provides a uniform minimum set of commands for controlling DCE function load/unload, requesting data set uplink/downlink, assessing node status. This interface also supports scripting and passthrough of commands to subsidiary DCE nodes (thus, an entire network can be initialized and parameterized from a single command script initiated at a top level node). Through this interface, drivers can be selected, initiated, and killed. Each driver can be loaded and initialized, can be started for collection, can be monitored (the real time uplink of data abridged to the capacity of the communication link), and buffers data into the shared memory/disk buffers for virtual data access throughout the network of nodes. When data collection is completed, the driver can be killed.

Drivers act as the interface between hardware devices and the object-abstracted data collection environment. Typically, drivers live on embedded DSPs or on small simple systems (like those running OS-9 or MS-DOS). In this environment, the driver directly attaches to hardware interrupts, read and write device registers, and makes the calls available in the Data Interface Library to encapsulate data items into object-oriented stream elements. From that point on, the standard DCE functionality takes over to distribute the data throughout the network. This principle of earlier possible data encapsulation can be violated for performance reasons, but is generally adhered to because it makes the rest of the data collection environment uniform and each data item independent. The Data Interface Library supports data collection bandwidth from the core MMDS physiological monitor and at up to 16,000 data items (float scalars) per second from a 486DX2 embedded processor attached to a local Intranet, it supports capture of real time video, packet/event capture, eye track data capture, serial data capture, etc (640×480, full color; nominally 1 mbyte per second) from a Pentium Pro 200 to a similar network connection. Thus, with adequate computational horsepower, full data encapsulation at the driver represents a reasonable approach to data abstraction.

It should be noted that many drivers are more abstract than direct hardware connections. For instance, a driver embedded in Unix systems can monitor network data packet traffic. Event monitors in Windows and Unix systems capture key, window, and mouse events to monitor operation of selected user interface applications. Drivers which read standard socket and serial streams can parse inputs from attached devices. In a satellite telemetry application currently under development, the driver reads data frames from the satellite down link, decommutate the data, and encapsulates it as though it came from an array of parallel analog input devices. Thus, inputs can be anything from video sequences, to a series of messages.

Another special function type is the viewer. While it is possible to control the DCE network through the command scripting language of a DCE node or through custom implemented functions, this approach provides a limited range of built-in data views. Control of a data collection and assimilation network is normally effected through a viewer. The Data View framework allows the user to connect to a DCE through an application designed to execute functions which generate data views and control interfaces. The Viewer framework provides the interfaces for selecting DCE nodes, feeding them scripts (and generating scripts from dialogs), checking status, and executing functions which perform analysis and/or create data displays. The viewer framework also provides interfaces to editors and language environments so that quick plug-in functions (in Perl, JAVA, etc.) can be created, edited, and attached to a DCE node for execution.

Viewers, or functions typically instantiated from within the Data Viewer framework, read data items from the environment through the Data Interface Library and present this data to the user in a viewer specific way. For instance, standard viewers include visualization of text message sequences (in a scrolling window similar to an X-term), Audio/video display windows (for video data streams), strip charts, bar graphs, spectrograms, etc. for numerical data streams, and specialized views for location, tracking, and physiological data streams. Users may implement application specific customized viewers easily because the basic framework is available as a template, and all data access functions are encapsulated within the Data Interchange Library. However, the GUI management functions associated with views are Unix or Win 32 platform dependent (X-based viewers can be executed on Win 32 platforms with an X-terminal task).

Figure 14:
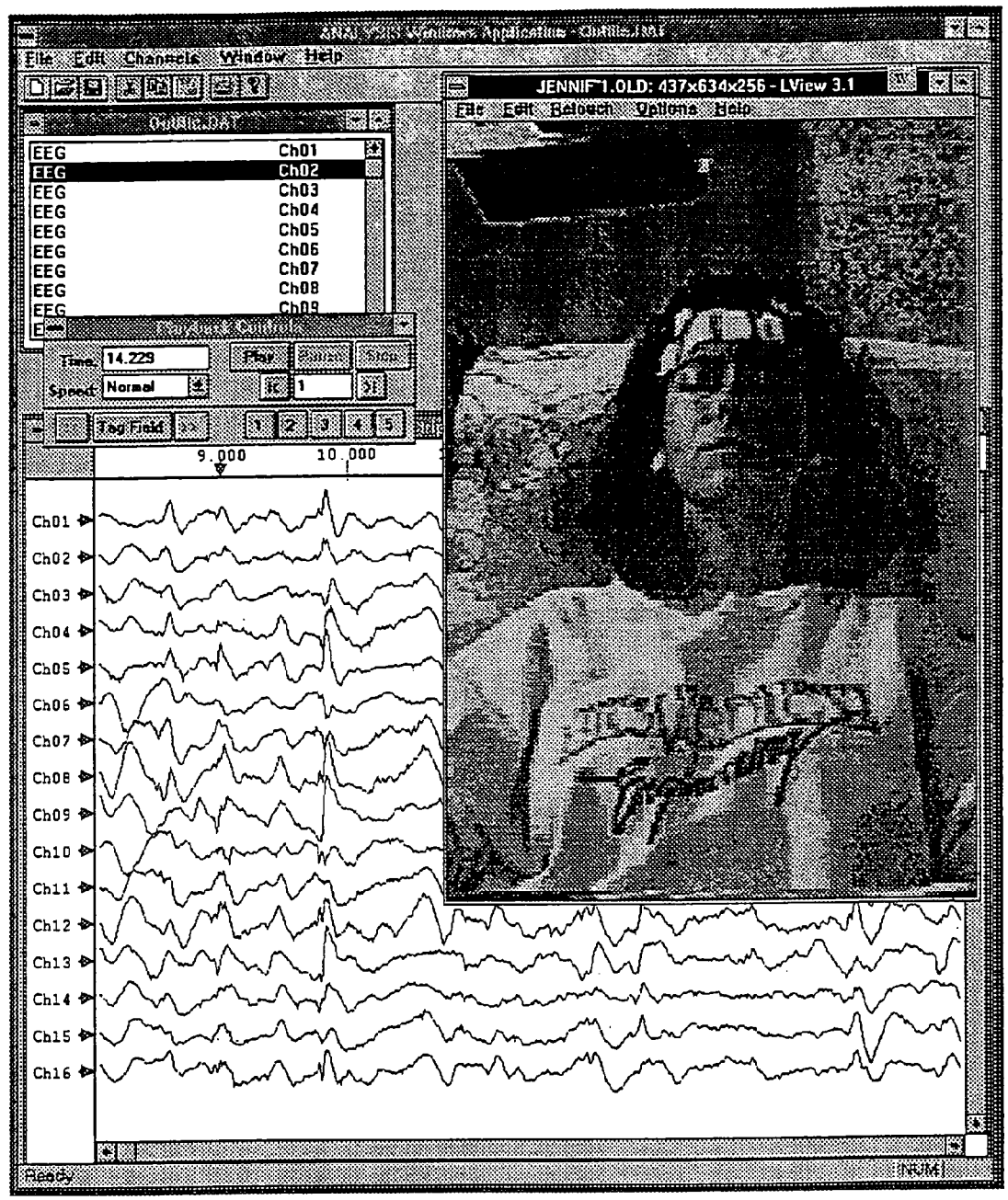
FIG. 14 is a screen display which shows command interface data plotted as a strip chart and video displayed in a video window.

The viewer framework also supports attached functions which accept time from the framework (in synchronization with displays). This allows the user to create synthesized data streams which are dynamically created through computation based on combinations of existing real streams. FIG. 14 shows some displays from the current implementation of the Data Viewing Environment. This view shows command interface, data plotted as a strip chart, and video (displayed in a video windows).

That claimed is:

1. A method of remotely monitoring a plurality of patients, comprising the steps of:
   configuring a plurality of data-collection environment (DCE) nodes into a hierarchical communications network architecture, each DCE node being operative to tag received physiologic data with time and source identifiers regarding the patient, or the source of origin of the data, and the time at which the data was collected, the DCE nodes including a plurality of patient-monitoring nodes and at least one data-viewing node, each patient-monitoring node including a portable, wearable monitor including one or more sensors, each sensor being operative to collect physiologic data at a data collection rate and at a data collection time;
   tagging the collected data with time and source identifiers so that the data are self-descriptive;
   packetizing the tagged data by segmenting the data into discrete packets;
   feeding the packetized data to the communications network; and
   wherein each data-viewing node enables a clinician to access and view the physiologic data from any other node in the communications network in a time-ordered manner even if the data arrived at a time, or in a time order, different than the time or order in which it was collected at the patient-monitoring nodes; and
   at least a portion of the hierarchical communications network architecture is wireless.

2. The method of claim 1, wherein at least a portion of the hierarchical communications network architecture utilizes the Internet.

3. The method of claim 1, further including the steps of encrypting the data prior to feeding it to the network; and decrypting the data prior to viewing.

4. The method of claim 1, further including the step of buffering the data at one or more of the DCE nodes.

5. A method of remotely monitoring a plurality of patients, comprising the steps of:
   configuring a plurality of data-collection environment (DCE) nodes into a hierarchical communications network architecture, each DCE node being operative to tag received physiologic data with time and source identifiers regarding the patient, or the source of origin of the data, and the time at which the data was collected, the DCE nodes including a plurality of patient-monitoring nodes and at least one data-viewing node, each patient-monitoring node including a portable, wearable monitor including one or more sensors, each sensor being operative to collect physiologic data at a data collection rate and at a data collection time;
   tagging the collected data with time and source identifiers so that the data are self-descriptive;
   packetizing the tagged data by segmenting the data into discrete packets;
   feeding the packetized data to the communications network;
   wherein each data-viewing node enables a clinician to access and view the physiologic data from any other node in the communications network in a time-ordered manner even if the data arrived at a time, or in a time order, different than the time or order in which it was collected at the patient-monitoring nodes; and
   wherein the data is cardiac-related.

6. A method of remotely monitoring a plurality of patients, comprising the steps of:
   configuring a plurality of data-collection environment (DCE) nodes into a hierarchical communications network architecture, each DCE node being operative to tag received physiologic data with time and source identifiers regarding the patient, or the source of origin of the data, and the time at which the data was collected, the DCE nodes including a plurality of patient-monitoring nodes and at least one data-viewing node, each patient-monitoring node including a portable, wearable monitor including one or more sensors, each sensor being operative to collect physiologic data at a data collection rate and at a data collection time;
   tagging the collected data with time and source identifiers so that the data are self-descriptive;
   packetizing the tagged data by segmenting the data into discrete packets;
   feeding the packetized data to the communications network;
   wherein each data-viewing node enables a clinician to access and view the physiologic data from any other node in the communications network in a time-ordered manner even if the data arrived at a time, or in a time order, different than the time or order in which it was collected at the patient-monitoring nodes; and
   wherein the data includes electrocardiogram information.

* * * * *